US010023335B2

(12) United States Patent
Gupta et al.

(10) Patent No.: US 10,023,335 B2
(45) Date of Patent: *Jul. 17, 2018

(54) FAST DISSOLVING PHARMACEUTICAL COMPOSITION

(71) Applicant: Ferring B.V., Hoofddorp (NL)

(72) Inventors: Shweta Gupta, Thane (IN); Varinder Ahuja, Mumbai-Maharashtra (IN); Tejas Gunjikar, Nashik-Maharashtra (IN); Kristin Wannerberger, Pully (CH)

(73) Assignee: Ferring B.V., Hoofddorp (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/571,883

(22) Filed: Dec. 16, 2014

(65) Prior Publication Data

US 2015/0150798 A1 Jun. 4, 2015

Related U.S. Application Data

(63) Continuation of application No. 13/636,758, filed as application No. PCT/EP2011/054699 on Mar. 28, 2011, now Pat. No. 8,946,153.

(30) Foreign Application Priority Data

Mar. 29, 2010 (IN) .............. 743/DEL/2010

(51) Int. Cl.
| | |
|---|---|
| *A61K 9/00* | (2006.01) |
| *B65B 31/04* | (2006.01) |
| *A61K 9/20* | (2006.01) |
| *A61K 31/4178* | (2006.01) |
| *A61K 31/426* | (2006.01) |
| *A61K 31/4545* | (2006.01) |
| *A61K 31/47* | (2006.01) |
| *A61K 38/11* | (2006.01) |
| *B65B 3/04* | (2006.01) |
| *B65B 63/08* | (2006.01) |
| *A61J 1/03* | (2006.01) |
| *A61K 38/22* | (2006.01) |
| *A61K 47/10* | (2017.01) |
| *A61K 47/12* | (2006.01) |
| *A61K 47/26* | (2006.01) |
| *A61K 47/36* | (2006.01) |
| *B65D 75/36* | (2006.01) |

(52) U.S. Cl.
CPC .............. *B65B 31/04* (2013.01); *A61J 1/035* (2013.01); *A61K 9/0002* (2013.01); *A61K 9/0056* (2013.01); *A61K 9/205* (2013.01); *A61K 9/2095* (2013.01); *A61K 31/4178* (2013.01); *A61K 31/426* (2013.01); *A61K 31/4545* (2013.01); *A61K 31/47* (2013.01); *A61K 38/11* (2013.01); *A61K 38/22* (2013.01); *A61K 47/10* (2013.01); *A61K 47/12* (2013.01); *A61K 47/26* (2013.01); *A61K 47/36* (2013.01); *B65B 3/04* (2013.01); *B65B 63/08* (2013.01); *B65D 75/367* (2013.01)

(58) Field of Classification Search
CPC .... A61K 38/00; A61K 31/702; A61K 31/715; A61K 31/733; A61K 8/73; A61K 2300/00; A61K 45/06; A61K 9/0053; A61K 9/19; A61K 38/10; A61K 38/14; A61K 9/006; A61K 31/00; A61K 35/00; A61K 47/48246; A61K 9/0056; A61K 9/48; A61K 2039/542; A61K 2039/55516; A61K 2800/92; A61K 38/02; A61K 38/08; A61K 38/18; A61K 38/22; A61K 39/00; A61K 9/2095; A61K 9/2893; A61K 9/4825; A61K 9/5052; A61K 2800/52; A23V 2250/5062; A23V 2250/28; A23V 2250/5046; A23L 1/30
See application file for complete search history.

(56) References Cited

U.S. PATENT DOCUMENTS

| | | | | |
|---|---|---|---|---|
| 4,260,602 | A * | 4/1981 | Moreno | ................. A61K 39/35 436/530 |
| 6,509,040 | B1 | 1/2003 | Murray et al. | |
| 7,560,429 | B2 | 7/2009 | Nilsson et al. | |
| 8,007,830 | B2 | 8/2011 | Down | |
| 8,158,152 | B2 | 4/2012 | Palepu | |
| 8,946,153 | B2 | 2/2015 | Gupta et al. | |
| 9,096,335 | B2 * | 8/2015 | Ahuja | .................. A61K 9/0056 |
| 2002/0177561 | A1 * | 11/2002 | Van Loo | .............. A61K 31/733 514/23 |

(Continued)

FOREIGN PATENT DOCUMENTS

| | | |
|---|---|---|
| CA | 2516291 | 9/2014 |
| CN | 1094282 A | 11/1994 |

(Continued)

OTHER PUBLICATIONS

Sugimoto et al. Effect of Formulated Ingredients on Rapidly Disintegrating Oral Tablets Prepared by the Crystalline Transition Method. Chem. Pharm. Bull. 54(2) 175-180 (2006).*
Merck Index Online (Ondansetron). https://www.rsc.org/Merck-Index/monograph/m8213/ondansetron?q=authorize Nov. 18, 2017.*
EPO Official Action issued in corresponding EP Application No. 11711321.7-1455 dated Jun. 4, 2015.
Krasnyuk et al., Farmatsevticheskaya tehnologiya; Tehnologiya lekarstvennykh form: Uchebnik dlya stud. Sred. Prof. ucheb. Zavedeniy. -M: Akademiya, pp. 464 (2004).
Office Action dated Apr. 2, 2015, U.S. Appl. No. 13/638,121.

(Continued)

*Primary Examiner* — Marcela M Cordero Garcia
*Assistant Examiner* — Jia-Hai Lee
(74) *Attorney, Agent, or Firm* — Finnegan, Henderson, Farabow, Garrett & Dunner LLP

(57) ABSTRACT

The subject invention is directed to a pharmaceutical composition comprising an open matrix network carrying a pharmaceutically active ingredient, wherein the open matrix network comprises levan.

19 Claims, No Drawings

(56) References Cited

U.S. PATENT DOCUMENTS

| | | | |
|---|---|---|---|
| 2004/0096569 A1 | 5/2004 | Barkalow et al. | |
| 2005/0266088 A1* | 12/2005 | Hinrichs | A61K 31/5513 424/488 |
| 2008/0044900 A1 | 2/2008 | Mooney et al. | |
| 2008/0241226 A1* | 10/2008 | Abeln | A23F 3/34 424/439 |
| 2009/0246257 A1 | 10/2009 | Modi | |
| 2010/0069320 A1* | 3/2010 | Speelmans | A23L 33/22 514/54 |
| 2012/0135050 A1 | 5/2012 | Dill | |
| 2013/0123179 A1 | 5/2013 | Gupta et al. | |
| 2013/0310319 A1 | 11/2013 | Ahuja et al. | |

FOREIGN PATENT DOCUMENTS

| | | | |
|---|---|---|---|
| CN | 1337876 | | 2/2002 |
| EP | 0958825 A1 | | 11/1999 |
| EP | 1308171 | | 5/2003 |
| EP | 1428526 | | 6/2004 |
| EP | 1514553 | | 3/2005 |
| EP | 1501534 | | 7/2006 |
| EP | 1757279 | | 2/2007 |
| GB | 1 548 022 | | 7/1979 |
| JP | 2006/511549 | | 4/2006 |
| WO | WO 00/25754 | | 5/2000 |
| WO | WO 00/27364 | | 5/2000 |
| WO | WO 00/44351 | | 8/2000 |
| WO | WO 2000/061117 A1 | | 10/2000 |
| WO | WO 00/78817 A1 | | 12/2000 |
| WO | WO 01/00182 | | 1/2001 |
| WO | WO 01/12161 A1 | | 2/2001 |
| WO | WO 2002/03992 | | 1/2002 |
| WO | WO 2003/082246 | | 10/2003 |
| WO | WO 2003/094886 A2 | | 11/2003 |
| WO | WO 2004/054546 A | | 7/2004 |
| WO | WO 2006/067593 A1 | | 6/2006 |
| WO | WO2006067593 | * | 6/2006 ............... A61K 9/00 |
| WO | WO 2007/143676 | | 12/2007 |
| WO | WO 2009/093785 A1 | | 7/2009 |
| WO | WO 2011/120904 A2 | | 10/2011 |

OTHER PUBLICATIONS

Russian Office Action dated May 21, 2015, in Russian Application No. 2012141140/15(066314).
Beine et al., "Directed Optimization of Biocatalytic Transflycosylation Processes by the Integration of Genetic Algorithms and Fermentative Approaches into a Kinetic Model", Process Biochemistry, Elsevier, NL, vol. 44, No. 10, pp. 1103-1114 (2009).
Combie, J., "Polysaccharides for Drug Delivery and Pharmaceutical Applications", Chapter 3, pp. 263-269, ISBN13: 9780841239609 (2006).
Co-Pending U.S. Appl. No. 13/636,758, filed Jan. 29, 2013 (Published May 16, 2013 as US 2013-0123179 A1).
Co-Pending U.S. Appl. No. 13/952,084, filed Jul. 25, 2013 (Published Nov. 21, 2013, US 2013-0310319 A1).
DDAVP Nasal Spray (Desmopressin Acetate), Sanofi-Aventis U.S. LLC., (2007).
EPO Official Action issued in corresponding EP Application No. 11711526.1-1455 dated Dec. 4, 2013.
International Preliminary Report on Patentability for PCT/EP2011/054698 dated Oct. 2, 2012.
International Preliminary Report on Patentability for PCT/EP2011/054699 dated Oct. 2, 2012.
International Search Report and Written Opinion for PCT/EP2011/054698 dated Mar. 9, 2012.
International Search Report and Written Opinion for PCT/EP2011/054699 dated Oct. 2, 2012.
Office Action (Final) dated May 8, 2014, in co-pending U.S. Appl. No. 13/952,084.
Office Action dated May 8, 2014, in co-pending U.S. Appl. No. 13/636,758.
Pleuvry, Barbara J., Drugs Acting by Causing Physicochemical Changes in the Enviroment Anaesthesia & Intensive Care Medicine, vol. 6, Issue 4, pp. 133-134, (Apr. 2005).
Shih et al., "Selective Production and Characterization of Levan by Bacillus Subtillis (Natto) Takahashi," J. Agric Food Chem. Oct. 19, 2005;53(21):8211-5.
Srinarong et al., "Strongly Enhanced Dissolotion Rate of Fenofibrate Solid Dispersion Tablets by Incorporation of Superdisintegrants", EP Journal of Pharmaceutics and Biopharmaceutics, Elsevier, 73(1):154-161 (Sep. 2009).
Sugimoto et al., "Effect of Formulated Ingredients on Rapidly Disintegrating Oral Tablets Prepared by the Chrstalline Transition Method", Chem Pharm Bull (Tokyo), 54(2):175-80, Feb. 2006.
Teva Pharmaceuticals USA, Desmopressin Acetate Tablet Product Description, (Feb. 2008).
Office Action (Final) dated Sep. 10, 2015, U.S. Appl. No. 13/638,121.
Office Action (non-final) dated Sep. 10, 2015, U.S. Appl. No. 14/343,285.
Office Action (non-final) dated May 13, 2016, U.S. Appl. No. 14/343,285.
Raes et al., "Retrospective Analysis of Efficacy and Tolerability of Tolterodine in Children with Overactive Bladder," European Urology 45 (2004) pp. 240-244.
Tsujimura et al., "Survey of Overactive Bladder Symptoms Influencing Bother Before and After Treatment With Tamsulosin Hydrochloride in Japanese Patients With Benign Prostatic Hyperplasia," Urology 78, 2011, pp. 1058-1062.
Chueshov et al., "Promyshlennaya tekhnologia lekarstv," UkrFA, Kharkov, Osnova, 1999, vol. 2. p. 353.
Office Action (final) dated Feb. 9, 2017, U.S. Appl. No. 14/443,759.
Office Action (non-final) dated Apr. 6, 2017, U.S. Appl. No. 13/638,121.
The Committee for Establishment of the Clinical Guidelines for Nocturia of the Neurogenic Bladder Society, "Clinical guidelines for nocturia," Int. J. Urology, 2010, vol. 17, pp. 397-409.

* cited by examiner

FAST DISSOLVING PHARMACEUTICAL COMPOSITION

This is a continuation of application Ser. No. 13/636,758, filed Jan. 29, 2013, which is a national stage entry application under § 371 of International Patent Application No. PCT/EP2011/054699, filed Mar. 28, 2011, and claims the priority benefit of Indian Application No. 743/DEL/2010, filed on Mar. 29, 2010, all of which are incorporated herein by reference.

FIELD OF THE INVENTION

The subject invention relates to fast dissolving pharmaceutical compositions, to methods of making them and to their use in the treatment and prophylaxis of diseases in mammals, particularly humans.

BACKGROUND OF THE INVENTION

Fast dissolving pharmaceutical dosage forms which are designed to release an active ingredient in the oral cavity are well known and can be used to deliver a wide range of drugs (*Critical Reviews in Therapeutic Drug Carrier Systems*, 21 (6):433-475 (2004); Seager H. (1998), *J. Phar. Pharmacol* 50:375-382; Bandari et al. (January 2008), *Asian Journal of Pharmaceutics* 2-11).

In a fast dissolving dosage form, a drug may physically be trapped in a matrix composed of e.g. mannitol and fish gelatin (EP 1501534; EP1165053), modified starch (U.S. Pat. No. 6,509,040), pullulan in combination with an amino acid (EP1803446), or maltodextrin in combination with sorbitol (US2004/0228919). The solution, suspension or dispersion of the drug and the carrier material may be filled into blister cavities, frozen and thereafter lyophilized. However, dosage forms produced in this manner are mostly fragile and brittle, have limited physical strength, and cannot withstand any pressure. In addition, dosage units so produced are difficult to pack and unpack.

SUMMARY OF THE INVENTION

The subject invention provides new fast dissolving oral pharmaceutical compositions typically in a unit dosage form, typically oral lyophilisates (also named orally disintegrating tablets). Fast dissolving dosage forms of the invention have relatively high tensile strength (i.e. force required to break a tablet in a three-point bending test) on the one hand and a fast disintegration/dissolution time on the other hand. This relatively high tensile strength permits, amongst others, to easily remove the composition from its container, typically a blister pack, without disintegration. The unit dosage form of the invention can typically be handled in a manner similar to that of a conventional compressed tablet, with disintegration occurring only upon contact with an aqueous liquid or with saliva within the mouth.

In one embodiment, the present invention provides a pharmaceutical composition comprising an open matrix network carrying a pharmaceutically active ingredient, wherein the open matrix network is comprised of levan.

In another embodiment, the present invention provides a pharmaceutical composition comprising a matrix carrying a pharmaceutically active ingredient, the matrix rapidly disintegrating upon contact with an aqueous solution or with saliva, said matrix comprising levan.

The pharmaceutical composition of the invention is unique in that it has a relatively high tensile strength, on the one hand, and a rapid dissolution in an aqueous medium or in saliva, on the other hand.

The relatively high tensile strength permits the handling of the composition in a manner similar to that of a regular compressed tablet including, in particular, removal from a package in which they are held, e.g. a blister pack, without risk of damaging the dosage form between the fingers. Notwithstanding this tensile strength, the composition of the invention disintegrates rapidly when contacted with an aqueous medium or with saliva, in particular the composition rapidly disintegrates when taken orally. The disintegration in an aqueous medium or in the oral cavity upon consumption (where it disintegrates upon contact with saliva) is typically within less than 30 seconds, and more typically within less than 10 seconds, at times less than 9, 8, 7, 6, 5, 4, 3, 2 or even 1 second.

Accordingly, the invention further provides a pharmaceutical composition comprising a pharmaceutically active ingredient, having a tensile strength so as to allow consumer handling of the composition (typically in a unit dosage form) in a manner similar to that of a compressed tablet, the pharmaceutical composition of the invention typically having a tensile strength ranging between about 0.05 to 1.6 N/mm$^2$ and a rapid dissolution rate such that at least 80% of the composition is disintegrated in an aqueous medium or in saliva in less than 30 seconds, at times less than 10 seconds and even less than 9, 8, 7, 6, 5, 4, 3, 2, or 1 second.

The pharmaceutical composition of the invention may be obtained by subliming a solvent (e.g. water), for example in a freeze drying process, from a liquid preparation that comprises the active ingredient and the matrix forming agent(s) in solution. According to one embodiment, unit dosage quantities of the liquid preparation are introduced into depressions and sublimation is then carried out thereby obtaining (after sublimation) a pharmaceutical composition in a unit dosage form. The depressions may be those of an open blister pack and following the sublimation step, and thereby the formation of the solid unit dosage form of the composition in the depression, a sealing film or foil is placed over the depressions to form a sealed blister pack.

The invention further provides a process for preparing a pharmaceutical composition that comprises subliming a solvent from a liquid preparation comprising a pharmaceutically active ingredient and levan in the solvent.

The invention also provides a process for the preparation of a pharmaceutical composition comprising (a) preparing a solution comprising levan and an active ingredient in a solvent; (b) freezing said solution; (c) subliming the solvent from the frozen solution, wherein the pharmaceutical composition so obtained is in fast-dispersing dosage form which disintegrates within less than 30 seconds upon contact with an aqueous solution or with saliva.

DETAILED DESCRIPTION OF THE INVENTION

The subject invention provides a fast-dissolving, typically orodispersible, pharmaceutical composition, usually prepared and provided in unit dosage form, typically an oral lyophilisate, comprising an active ingredient and one or more excipients. At least one of the excipients, normally the main matrix forming agent, is the polysaccharide levan.

The following are some of the terms used above and below in this patent specification and claims:

The terms "active ingredient" or "pharmaceutically active ingredient" will be used interchangeably herein.

The term "pharmaceutical composition" and "composition" are interchangeably used herein to refer to a pharmaceutical composition of the invention.

The term "unit dosage form" or "dosage form" will be used herein to refer to said composition which is formulated with an amount of an active pharmaceutical ingredient (API) in a dose for administration as a single dose to a target individual. The unit dosage form may be adapted, depending on the nature of the active ingredient, the indication, the disease stage and various other factors known per se for once, twice, thrice or any other number of daily administrations.

The term "carrying" should be understood to encompass any form of interaction between an active ingredient and the matrix that allows the matrix to hold and/or contain an amount of active ingredient and release it to the aqueous medium or to saliva upon disintegration of the matrix.

The term "matrix" should be understood to denote a solid carrier medium for an active ingredient. The matrix comprises one or more excipients. The excipients that form the matrix may be referred to herein, at times, as "matrix forming agents" and each of said agents as "matrix forming agent".

The term "an open matrix network" should be understood to encompass a matrix of water-soluble or water-dispersible carrier material (matrix-forming agent(s)) having interstices dispersed throughout. The matrix rapidly disintegrates upon contact with an aqueous solution or with saliva.

In one embodiment, levan is the sole matrix forming agent in the composition. In another embodiment, one or more secondary matrix forming agents may be present in the composition.

Non-limiting examples of sugars, sugar alcohols, monosaccharides, disaccharides, trisaccharides, polysaccharides, proteins, amino acids, gums and the like, which are useful as secondary matrix forming agents, include without limitation, mannitol, trehalose, raffinose, inositol, pullulan, sucrose, lactose, dextrose, erythritol, xylitol, lactitol, maltitol, isomalt, alanine, arginine, threonine, glycine, cysteine, serine, histidine, valine, proline, lysine, asparagine, glutamine, ribose, glucose, galactose, fructose, maltose, maltotriose, guargum, xanthan gum, tragacanth gum, veegum and so forth.

Generally, the balance of the formulation can be matrix. Thus the percentage of the levan matrix can approach 100%. The amount of the secondary matrix forming agent useful in accordance with the present invention may range from about 0 to about 90%.

In one embodiment of the invention, levan is the main matrix forming agent in the composition. In another embodiment, the composition further comprises mannitol or raffinose or trehalose or combinations thereof as secondary matrix forming agent.

In one embodiment, levan is the matrix forming agent, comprising 10-99.99% out of the entire weight of the composition. In another embodiment, levan comprises 30-75% out of the entire weight of the composition. In yet another embodiment, levan comprises 40-70% out of the entire weight of the composition. In yet another embodiment, levan comprises 50-65% out of the entire weight of the composition.

In other embodiments, mannitol or trehalose or raffinose or combinations thereof are used as secondary matrix forming agents, comprising 0-89.99% out of the entire weight of the composition. In one embodiment, these secondary matrix forming agents comprise 15-50% out of the entire weight of the composition. In another embodiment, these secondary matrix forming agents comprise 25-50% out of the entire weight of the composition.

Thus, a composition of the invention can be one comprising levan as the main matrix-forming agent and mannitol or trehalose or raffinose (or combinations thereof) as secondary matrix-forming agent, with levan constituting 10-99.99% (all % of ingredient are w/w, meaning weight of mentioned ingredient out of the weight of all constituents of the composition combined), and the secondary matrix forming agent constituting 0-89.99%, typically 25-50%. The content of the active ingredient may typically (but not exclusively) be up to 90% of the entire composition, typically in the range of 0.01-70% depending on the nature of the active ingredient. In one embodiment, the active ingredient comprises 0.01-1% out of the entire weight of the composition. In another embodiment, the active ingredient comprises 0.5-2% out of the entire weight of the composition. In yet another embodiment, the active ingredient comprises 5-30% out of the entire weight of the composition. In other embodiments, the active ingredient comprises 20-40% out of the entire weight of the composition. In yet other embodiments, the active ingredient comprises 60-90% out of the entire weight of the composition.

In one embodiment, the composition of the invention does not contain fish gelatin. In another embodiment, the composition of the invention does not contain a modified starch. In another embodiment, the composition of the invention does not contain pullulan in combination with an amino acid. In another embodiment, the composition of the invention does not contain maltodextrin in combination with sorbitol.

"Disintegration Time" and "Dissolution Time" are used interchangeably herein and should be understood to mean the time needed to dissolve or disintegrate the composition of the invention in an aqueous solution or with saliva within the oral cavity.

"Oral dissolving Time" as used herein should be understood to mean the time needed to dissolve the composition of the invention in the oral cavity.

"Rapid/Fast disintegration/dissolution" as used herein should be understood to encompass disintegration of at least 80% of the composition of the invention, typically 90% and more typically 100% of the composition in an aqueous medium or in saliva (in the oral cavity) within 30 seconds, typically within 10 seconds and at times even within 9, 8, 7, 6, 5, 4, 3, 2 or 1 second.

Examples of an aqueous medium as used herein are water or a buffer (e.g. potassium dihydrogen phosphate, dipotassium hydrogen phosphate, sodium hydrogen phosphate) or artificial saliva as described by Morjaria et. al (May 2004), *Dissolution Technologies* 12-15.

Saliva as used herein refers to the saliva in the oral cavity of a mammal, in particular a human.

"Tensile strength" as used herein should be understood to be the force required to break a tablet, which is measured by the three-point bending test, wherein the tablet is subjected to a bending stress (Mohd et al. (2002), *Drug Development and Industrial Pharmacy* 28 (7):809-813).

In one embodiment, a pharmaceutical composition of the invention has a tensile strength in the range of about 0.05-1.6 $N/mm^2$. In another embodiment, a pharmaceutical composition of the invention has a tensile strength in the range of about 0.15-1.4 $N/mm^2$. In yet another embodiment, a pharmaceutical composition of the invention has a tensile strength in the range of about 0.3-0.85 $N/mm^2$.

It is envisaged that a pharmaceutical composition of the invention has a rapid disintegration/dissolution rate such that at least 80% of the composition is dissolved in an aqueous medium or in saliva within 30 seconds, typically within 10 seconds. In one embodiment, a pharmaceutical composition of the invention has a rapid disintegration/dissolution rate such that at least 90% of the composition is dissolved in an aqueous medium or in saliva within 30 seconds, typically within 10 seconds.

In one embodiment, a pharmaceutical composition of the invention has a tensile strength in the range of about 0.05-1.6 N/mm$^2$ and a rapid disintegration/dissolution rate such that at least 80% of the composition is dissolved in an aqueous medium or in saliva within 30 seconds, typically within 10 seconds.

In another embodiment, the invention provides a pharmaceutical composition comprising a pharmaceutically active ingredient, having a tensile strength ranging between about 0.15 to 1.4 N/mm$^2$ and a rapid disintegration/dissolution rate such that at least 80% of the composition is dissolved in an aqueous medium or in saliva within 30 seconds, typically within 10 seconds.

In another embodiment, the invention provides a pharmaceutical composition comprising a pharmaceutically active ingredient, having a tensile strength ranging between about 0.3 to 0.85 N/mm$^2$ and a rapid disintegration/dissolution rate such that at least 80% of the composition is dissolved in an aqueous medium or in saliva within 30 seconds, typically within 10 seconds.

In one embodiment, a pharmaceutical composition of the invention has a tensile strength in the range of about 0.05-1.6 N/mm$^2$ and a rapid disintegration/dissolution rate such that at least 90% of the composition is dissolved in an aqueous medium or in saliva within 30 seconds, typically within 10 seconds.

In another embodiment, the invention provides a pharmaceutical composition comprising a pharmaceutically active ingredient, having a tensile strength ranging between about 0.15 to 1.4 N/mm$^2$ and a rapid disintegration/dissolution rate such that at least 90% of the composition is dissolved in an aqueous medium or in saliva within 30 seconds, typically within 10 seconds.

In another embodiment, the invention provides a pharmaceutical composition comprising a pharmaceutically active ingredient, having a tensile strength ranging between about 0.3 to 0.85 N/mm$^2$ and a rapid disintegration/dissolution rate such that at least 90% of the composition is dissolved in an aqueous medium or in saliva within 30 seconds, typically within 10 seconds.

The open matrix network enables a liquid to enter the dosage form through the interstices and permeate through its interior. Permeation by aqueous media (such as saliva, water, etc.) exposes the carrier material of both the interior and exterior of the dosage form to the action of the aqueous media or saliva whereby the network of carrier material is rapidly disintegrated/dissolved.

The open matrix structure is of a porous nature and enhances disintegration of the dosage form as compared with ordinary solid shaped pharmaceutical dosage forms such as (granulated and compressed) tablets, pills, capsules, suppositories and pessaries. Rapid disintegration results in rapid release of the active ingredient carried by the matrix.

In the subject invention, the carrier material of the open matrix network is levan or a derivative thereof.

Levan (also named leaven, levulosan, polyfructosan, polyfructose and polylevulan) is a polymer of fructose $C_6H_{12}O_6$. Levan is a polysaccharide with β-(2->6) linkages between the fructose rings where the numbers describe the carbon atoms in the fructose ring which are linked and the β describes the stereochemical relationship. Levans have also been described as fructans in which the predominant glycosidic linkage between the D-fructofuranoside monomeric units is β-(2->6). The levans are generally made by microorganisms and do not occur as high molecular weight compounds in plants. Some low molecular weight levans having a molecular weight of less than 100,000 Daltons can occur in grasses.

"Levan" as used herein should be understood to encompass levan derived from any source such as but not limited to *A. indicus, A. versicolor, Acetobacter suboxydans, Achromobacter* spp., *Actinomycenes* sp., *Actinomyces viscosus, Aerobacter aerogenes, Aerobacter levanicum, Aspergillus sydowi, Azotobacter chroococcum, Bacillus polymyxa, Bacillus licheniformis, Bacillus macerans, Bacillus megatherium, Bacillus mesentericus, Bacillus subtilis, Bacillus vulgatus, Corynebacterium laevaniformans, Erwinia herbicola, Gluconobacter oxydans, Leuconostoc mesenteroides, Odontomyces viscosus, Phytobacterium vitrosum, Phytomonas pruni, Psuedomonas Fluorescens, Pseudomonas Syringae, Pseudomonas prunicola, Rothis dentocariosa, Serratia kiliensis, Steptococcus bovis, Steptococcus mutans, Steptococcus salivarius, Xanthomonas campestris, Xanthomonas pruni, Zymomonas mobilis* and so forth. In a specific embodiment, the levan is obtained from *Zymomonas* and *Bacillus* species. In a more specific embodiment, the levan is obtained from *Zymomonas mobilis*.

It should be understood that also derivatives of levan (e.g. as described in WO98/03184) can be used in place of levan.

The pharmaceutically active ingredient may encompass any pharmaceutical ingredient such as a drug, a compound, a peptide, a nucleotide, and so forth.

Non-limiting examples of drugs which can be carried by the open matrix network of the subject invention are analgesics, alpha blockers, anti-allergy, anti-asthma, (allergic rhinitis, chronic uticaria), anti-inflammatory, antacids, anthelmintics, anti-arrhythmic agents, anti-arthritis, anti-bacterial, anti-anxiety, anti-coagulants, anti-depressants, anti-diabetics, anti-diarrheals, anti-diuretics, anti-epileptics, anti-fungal, anti-gout, anti-hypertensive, anti-incontinence, anti-insomnia, anti-malarials, anti-migraine, anti-muscarinic, anti-neoplastic and immunosuppressants, anti-protozoal, anti-rheumatics, anti-rhinitis, anti-spasmatic. anti-thyroid, antivirals, anxiolytics, sedatives, hypnotics and neuroleptics, beta-blockers, anti-benign hyperplasia (BHP), cardiac inotropic, corticosteroids, cough suppressants, cytotoxics, decongestants, diabetic gastric stasis, diuretics, enzymes, anti-parkinsonian, gastro-intestinal, histamine receptor antagonists, infertility, endometriosis, hormone replacement therapy, lipid regulating agents, local anesthetics, neuromuscular agents, nitrates and anti-anginal agents, menstrual disorders, motion sickness, anti-pain, anti-nausea, movement disorders, nutritional agents, opioid analgesics, oral vaccines, proteins, peptides and recombinant drugs, prevention of chemotherapy induced and post operative nausea and vomiting proton pump inhibitors, schizoprenia, sex hormones and contraceptives, seizure/panic disorder, sexual dysfunction (male and female), spermicides, stimulants voiding dysfunctions, veterinary medicines and so forth.

Specific non-limiting examples of these drugs are:

Alfa blockers: Tamsulosine

Analgesics and anti-Inflammatory agents: aspirin, aloxiprin, auranofin, azapropazone, benorylate, diflunisal, etodolac, fenbufen, fenoprofen calcium, flurbiprofen, ibuprofen, indomethacin, ketoprofen, meclofenamic acid, mefenamic acid, nabumetone, naproxen, oxaprozin, oxyphenbutazone, phenylbutazone, piroxicam, sulindac, paracetamol.

Antacids: aluminum hydroxide, magnesium carbonate, magnesium trisilicate, hydrotalcite, dimethicone.

Anthelmintics: albendazole, bephenium hydroxynaphthoate, cambendazole, dichlorophen, ivermectin, mebendazole, oxamniquine, oxfendazole, oxantel embonate, praziquantel, pyrantel embonate, thiabendazole.

Anti-allergic: des loratidine, loratidine, Montelukast, Montelukast sodium, Cetirizin, Fexofenadin, Ebastine.

Anti-arrhythmic agents: amiodarone HCl, disopyramide, flecainide acetate, quinidine sulphate.

Anti-bacterial agents: benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim.

Anti-coagulants: dicoumarol, dipyridamole, nicoumalone, phenindione.

Anti-depressants: amoxapine, ciclazindol, maprotiline HCl, mianserin HCl, nortriptyline HCl, trazodone HCl, trimipramine maleate.

Anti-diabetics: acetohexamide, chlorpropamide, glibenclamide, gliclazide, glipizide, tolazamide, tolbutamide.

Anti-diarrheals: atropine sulphate, codeine phosphate, cophenotrope, difenoxin, loperamide hydrochloride, suphasolazine, mesalazine, olsalazine, corticosteroids, prednisolone.

Anti-diuretics: desmopressin, desmopressin acetate.

Anti-epileptics: beclamide, carbamazepine, clonazepam, ethotoin, methoin, methsuximide, methyiphenobarbitone, oxcarbazepine, paramethadione, phenacemide, phenobarbitone, phenytoin, phensuximidc, primidone, sulthiame, valproic acid.

Anti-fungal agents: amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCl, terconazole, tioconazole, undecenoic acid.

Anti-gout agents: allopurinol, probenecid, sulphinpyrazone.

Anti-hypertensive agents: amlopidine, benidipine, darodipine, dilitazem HCl, diazoxide, felodipine, guanabenz acetate, indoramin, isradipine, minoxidil, nicardipine HCl, nifedipine, nimodipine, phenoxybenzamine HCl, prazosin HCl, reserpine, terazosin HCl.

Anti-insomnia: Zolpidem

Anti-malaria: amodiaquine, chloroquine, chloroproguanil HCl, halofantrine HCl, mefloquine HCl, proguanil HCl, pyrimethamine, quinine sulphate.

Anti-migraine agents: rizatriptan, dihydroergotamine mesylate, ergotamine tartrate, methysergide maleate, pizotifen maleate, sumatriptan succinate, caffeine.

Anti-muscarinic agents: oxybutinin, tolterodin, atropine, benzhexol HCl, biperiden, ethopropazine HCl, hyoscine butyl bromide, hyoscyamine, mepenzolate bromide, orphenadrine, oxyphencylcimine HCl, tropicamide.

Anti-neoplastic agents and Immunosuppressants: aminoglutethimide, amsacrine, azathioprene, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone.

Anti-protozoal agents: benznidazole, clioquinol, decoquinate, diiodohydroxyquinoline, diloxanide furcate, dinitolmide, furzolidone, metronidazole, nimorazole, nitrofurazone, ornidazole, tinidazole.

Anti-rheumatics: ibuprofen, aceclofenac, acemetacin, azapropazone, diclofenac sodium, diflunisal, etodolac, ketoprofen, indomethacin, mefenamic acid, naproxen, piroxicam, aspirin, benorylate, auranofin, penicillamine.

Anti-rhinitis, anti-uticaria: Cetirizin, fexofenadin, ebastine, loratidin, montelukast Anti-spasmatic: phloroglucinol anhydre Anti-thyroid agents: carbimazole, propylthiouracil.

Antivirals: acyclovir, amantadine hydrochloride, famciclovir, zidovadine, didanosine, zalcitabine, foscarnet sodium.

Anxiolytic, sedatives, hypnotics and neuroleptics: alprazolam, amylobarbitone, barbitone, bentazepam, bromazepam, bromperidol, brotizolam, butobarbitone, carbromal, chlordiazepoxide, Chlorpheniramine, chlormethiazole, chlorpromazine, clobazam, clonazepan, clotiazepam, clozapine, diazepam, droperidol, ethinamate, flunanisone, flunitrazepam, fluopromazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine phenylephrine, pimozide, prochlorperazine, pseudoephedrine HCL, sulpride, temazepam, thioridazine, triazolam, zopiclone.

β-Blockers: acebutolol, alprenolol, atenolol, labetalol, metoprolol, nadolol, oxprenolol, pindolol, propanolol.

Cardiac inotropic agents: amrinonc, digitoxin, digoxin, enoximone, lanatoside C, medigoxin.

Corticosteroids: beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone.

Cough suppressants: codeine phosphate dexomethorphan, guaifenesin, pholcodine, diamorphine, methadone.

Cytotoxics: ifosfamide, chlorambucil, melphalan, busulphan, cytotoxic antibodies, doxorubicin, epirubicin, plicamycin, bleomycin, methotrexate, cytarabine, fludarabine, gencitabine, fluorouracil, mercaptopurine, thioguanine, vincristine, vinblastine, vindesine, etoposide.

Decongestants: pseudoephedrine hydrochloride.

Diuretics: acetazolamide, amiloride, bendrofluazide, bumetanide, chlorothiazide, chlorthalidone, ethacrynic acid, frusemide, metolazone, spironolactone, triamterene.

Enzymes: pancreatin, pepsin, lipase.

Epilepsy: Gabapentin

Anti-parkinsonian agents: bromocriptine mesylate, lysuride maleate, selegiline, para-fluoroselegiline, lazabemide, rasagiline, 2-BUMP [N-(2-butyl)-N-methylpropargylamine], M-2-PP [N-methyl-N-(2-pentyl)-propargylamine], MDL-72145 [beta-(fluoromethylene)-3,4 -dimethoxy-benzeneethanamine], mofegiline, apomorphine, N-propylnoraporphine, cabergoline, metergoline, naxagolide, pergolide, piribedil, ropinirole, terguride, quinagolide.

Gastro-intestinal agents: bisacodyl, cimetidine, cisapride, diphenoxylate HCl, domperidone, metoclopramide, famotidine, loperamide, mesalazine, nizatidine, esomeprazole, metopimazinc, pantoprazole, ondansetron HCl, Granisetron, tropisetron, dolasetron, ranitidine HCl, sulphasalazine. Lanzoprazole, Histamine Receptor Antagonists: acrivastine, astemizole, cinnarizine, cyclizine, cyproheptadine HCl, dimenhydrinate, flunarizine HCl, loratadine, meclozine HCl, oxatomide, terfenadine, triprolidine.

Hormone replacement therapy: dydrogesterone

Hypertension: Enalapril

Lactation: Oxytocin, oxytocin agonists

Lipid regulating agents: bezafibrate, clofibrate, fenofibrate, gemfibrozil, probucol.

Local anaesthetics: amethocaine, amylocaine, benzocaine, bucricaine, bupivacaine, butacaine, butanilicaine, butoxycaine, butyl aminobenzoate, carticaine, chloroprocaine, cinchocaine, clibucaine, clormecaine, coca, cocaine, cyclomethycaine, dimethisoquin, diperodon, dyclocaine, ethyl chloride, ethyl p-piperidinoacetylaminobenzoate, etidocaine, hexylcaine, isobutamben, ketocaine, lignocaine, mepivacaine, meprylcaine, myrtecaine, octacaine, oxethazaine, oxybuprocaine, parethoxycaine, pramoxine, prilocaine, procaine, propranocaine, propoxycaine, proxymetacaine, ropivacaine, tolycaine, tricaine, trimecaine, vadocaine.

Motion sickness: diphenhydramine

Neuro-muscular agents: pyridostigmine.

Nitrates and other anti-anginal agents: amyl nitrate, glyceryl trinitrate, isosorbide dinitrate, isosorbide mononitrate, pentaerythritol tetranitrate.

Nutritional agents: betacarotene, vitamins, such as vitamin A, vitamin $B_2$, vitamin D, vitamin E, vitamin K, minerals.

Opioid analgesics: codeine, dextropropyoxyphene, diamorphme, dihydrocodeine, meptazinol, methadone, morphine, nalbuphine, pentazocine.

Oral vaccines: to prevent or reduce the symptoms of diseases such as Influenza, Tuberculosis, Meningitis, Hepatitis, Whooping Cough, Polio, Tetanus, Diphtheria, Malaria, Cholera, Herpes, Typhoid, HIV, AIDS, Measles, Lyme disease, Traveller's Diarrhea, Hepatitis A, B and C, Otitis Media, Dengue Fever, Rabies, Parainfluenza, Rubella, Yellow Lever, Dysentery, Legionnaires Disease, Toxoplasmosis, Q-Fever, Haemorrhegic Fever, Argentina Haemorrhegic Fever, Caries, Chagas Disease, Urinary Tract Infection caused by *E. coli*, Pneumococcal Disease, Mumps, Chikungunya, Hayfever, Asthma, Rheumatoid Arthritis, Carcinomas, Coccidiosis, Newcastle Disease, Enzootic pneumonia, Feline leukemia, Atrophic rhinitis, Erysipelas, Foot and Mouth disease and Swine pneumonia, or to prevent or reduce the symptoms of diseases caused by *Vibrio* species, *Salmonella* species, *Bordetella* species, *Haemophilus* species, Toxoplasmosis gondii, Cytomegalovirus, *Chlamydia* species, *Streptococcal* species, Norwalk Virus, *Escherischia coli, Helicobacter pylori*, Rotavirus, Neisseria gonorrhae, Neisseria meningiditis, Adenovirus, Epstein Barr Virus, Japanese Encephalitis Virus, Pneumocystis carini, Herpes simplex, Clostridia species, Respiratory Syncytial Virus, *Klebsiella* species, *Shigella* species, *Pseudomonas aeruginosa*, Parvovirus, *Campylobacter* species, *Rickettsia* species, *Varicella zoster, Yersinia* species, Ross River Virus, J.C. Virus, *Rhodococcus equi, Moraxella catarrhalis, Borrelia burgdorferi* and *Pasteurella haemolytica*.

Voiding dysfunctions: Tamsulosine, trospium chloride, tolterodine, oxybutinin

Proteins, peptides and recombinant drugs: recombinant hormones and iso-hormones, recombinant cytokines, recombinant plasminogens, TNF receptor fusion protein, monoclonal antibodies, nucleic acids, antisense oligonucleotides, oligonucleotides, glycoproteins and adhesion molecules.

Veterinary Arthiritis: Tepoxalin

Sex hormones and Contraceptives: clomiphene citrate, danazol, desogestrel, ethinyloestradiol, ethynodiol, ethynodiol diacetate, levonorgestrel, medroxyprogesterone acetate, mestranol, methyltestosterone, norethisterone, norethisterone enanthate, norgestrel, estradiol, conjugated estrogens, dydrogesterone, progesterone, stanozolol, stilboestrol, testosterone, tibolone.

Schizoprenia; Olanzapine, Nicergoline

Sexual dysfunction: Cabergolin, oxytocin, tadalafil, sildenafil, vardenafil

Spermicides: nonoxynol 9.

Stimulants: amphetamine, dexamphetamine, dexfenfluramine, fenfluramine, mazindol, pemoline.

In a specific, non-limiting embodiment, the active ingredient is desmopressin acetate. In this embodiment the dosage form can be used in voiding postponement or in the treatment or prevention of incontinence, primary nocturnal enuresis (PNE), nocturia or central diabetes insipidus. In one embodiment, the amount of desmopressin acetate in the composition comprises 0.01-2.00% w/w. In another embodiment, the amount of desmopressin acetate in the composition comprises 0.04-1.00% w/w.

In a specific, non-limiting embodiment, the active ingredient is loratidine. In this embodiment the dosage form can be used e.g. for the relief of nasal or non-nasal symptoms of allergic rhinitis and chronic idiopathic urticaria. In one embodiment, the amount of loratidine in the composition comprises 20-40% w/w. In another embodiment, the amount of loratidine in the composition comprises about 25-40% w/w.

In a specific, non-limiting embodiment, the active ingredient is famotidine. In this embodiment the dosage form can be used e.g. in the treatment of gastroesophageal reflux disease, duodenal and gastric ulcer, pathological hypersecretory conditions (e.g. Zollinger-Ellison syndrome and multiple endocrine adenomas). In one embodiment, the amount of famotidine in the composition comprises 50-90% w/w. In another embodiment, the amount of famotidine in the composition comprises 60-90% w/w.

In a specific, non-limiting embodiment, the active ingredient is montelukast sodium. In this embodiment the dosage form can be used e.g. in prophylaxis and chronic treatment of asthma, allergic rhinitis and exercise-induced bronchoconstriction. In one embodiment, the amount of montelukast sodium in the composition comprises 5-40% w/w. In another embodiment, the amount of montelukast sodium in the composition comprises 5-30% w/w.

In a specific, non-limiting embodiment, the active ingredient is ondansetron. In this embodiment the dosage form can be used e.g. in the prevention of postoperative nausea and/or vomiting and also in the prevention of nausea and/or associated with cancer chemotherapy and radiotherapy. In one embodiment, the amount of ondansetron in the composition comprises 10-30% w/w. In another embodiment, the amount of ondansetron in the composition comprises about 20% w/w.

A pharmaceutical dosage form of the invention disintegrates, thereby releasing the active ingredient, upon contact with a fluid (an aqueous medium or saliva).

Typically, a pharmaceutical dosage form of the invention is an orodispersible pharmaceutical dosage form which disintegrates in the mouth within 30 seconds, typically 10 seconds or less.

The term "orodispersible" as used herein should be understood to encompass a solid dosage form which disintegrates or dissolves in the mouth within (at most) 30 seconds. In further embodiments, the orodispersible dosage form disperses in the mouth within 10, 9, 8, 7, 6, 5, 4, 3, 2, or even within 1 second.

A suitable route of administration for the dosage form of the subject invention is oral administration including buccal and sublingual administration. In a specific embodiment, the dosage form is administered sublingually. Dosage forms of the invention may also be placed on the tongue or against the cheek or gingiva.

Pharmaceutical dosage forms of the present invention are adapted to supply the active ingredient to e.g. the oral cavity. The active may be absorbed across the mucosa at the site of administration, e.g. sublingual mucosa, and/or otherwise, in the case of oral administration, from the oral cavity (e.g. across the buccal and/or gingival mucosa) and/or from the gastrointestinal tract for systemic distribution.

The exact dose and regimen of administration of the dosage form will necessarily be dependent upon the therapeutic effect to be achieved and may vary with the particular active ingredient, the route of administration, and the age and condition of the individual subject to whom the medicament is to be administered. At times patients may be instructed to take two or any other number of unit dosage forms in a single administration or at times only a portion, such as half or a quarter of the unit dosage form in a single administration.

The dosage form of the invention achieves a balance of performance: tensile strength, stability and fast disintegration. It may be produced by known lyophilisate technology. It can be stored (and packed) in blisters but due to its tensile strength, can also be stored and/or packaged in bottles or bulk. The invention achieves these results in a single processing step, without the need to resort to multiple steps including granulation.

In addition to the ingredients previously discussed, the matrix may also include other excipients (auxiliary agents, accessory agents) such as, but not limited to fillers, matrix-forming agents, thickeners (including but not limited to guar gum and xanthum gum), binders, diluents, lubricants, pH adjusting agents, protecting agents, viscosity enhancers, wicking agents, non-effervescent disintegrants, effervescent disintegrants, surfactants, anti-oxidants, wetting agents, colorants, flavouring agents, taste-masking agents, sweeteners, preservatives and so forth.

In one embodiment, a composition of the invention is obtainable by subliming solvent from a liquid preparation comprising an active Ingredient, levan and optionally secondary matrix forming agent(s) in a solvent. Typically, the liquid preparation is placed in a mould, e.g. such that following sublimination a solid composition, typically in a dosage unit, is formed within the mould. The mould can be an open blister pack whereby the solid dosage unit is formed within the blister pack's depression which is thereafter sealed by a sealing film or foil.

In one embodiment, the process comprises introducing unit dosage quantities of said preparation into depressions of an open blister pack; and then subliming the preparation to obtain solid dosage forms within said depressions.

The sublimation can be earned out by freeze drying the preparation comprising the active ingredient, levan and optionally secondary matrix forming agent(s) in a solvent. In one embodiment, the solvent is water.

The invention thus discloses a process for preparing fast-dispersing dosage forms by lyophilizing a combination of an active ingredient, levan and optionally secondary matrix forming agent(s). The fast-dispersing dosage form contains a network of the active ingredient and the carrier levan and optionally the secondary matrix forming agent(s), the network having been obtained by subliming solvent from the liquid preparation that contains the active ingredient, levan and the other optional matrix forming agents. Said preparation may be a solution, suspension or dispersion.

Typically, an initial preparation comprising an active ingredient, levan and optionally secondary matrix forming agent(s) in a solvent is prepared, followed by sublimation. The sublimation can be carried out by freeze drying the preparation.

In a freeze drying procedure, the preparation (in liquid form) that comprises an active ingredient, levan and any other optional matrix forming agent in a solvent is filled into moulds. Each mould typically contains a defined amount of such solution with a defined amount of active ingredient. The preparation in the mould is then frozen, for example by passing gaseous cooling medium over the mould. After the preparation has been frozen, the solvent is sublimed therefrom. The sublimation is carried out in a freeze dryer. In consequence an open matrix network of levan optionally together with other matrix forming agents included in the solution, carrying the active ingredient, is thereby formed.

The preparation is contained in a mould during the freeze-drying process to produce a solid form in any desired shape. Prior to the lyophilization, the mould may be cooled and frozen (e.g. in a fast-freeze tunnel or on the shelves of the lyophilizer), for example using liquid nitrogen or solid carbon dioxide. In one embodiment, the freezing rate is from 0.1 to 2° C./minute. In another embodiment, the freezing rate is from 0.5 to 1.5° C./minute. In yet another embodiment, the freezing rate is from 10 to 260° C./minute. In another embodiment, the freezing rate is from 20 to 260° C./minute. In a further embodiment, the freezing rate is from 20 to 160° C./minute.

After lyophilization, the freeze dried compositions can either be removed from the mould if desired or stored therein until later use. Typically, each mould is so designed so to produce a unit dosage form of the composition. The composition so obtained is fast-dispersing and disintegrates within at most 30 seconds upon contact with fluid, typically within less than 10 seconds.

The solvent is typically water but may optionally also contain a co-solvent (such as an alcohol e.g. tert-butyl alcohol) to improve the solubility of the chemical.

The composition may contain a pH adjusting agent to adjust the pH of a solution from which the dosage form is prepared within the range of from 2 to 10, typically from 3.5 to 9.5 or from 4.5 to 8. Citric acid, sodium hydroxide, and sodium carbonate can be used as pH adjusting agent, but others including hydrochloric acid and malic acid can also be used. Non-volatile pH adjusting agents will not be removed by freeze drying or other sublimation processes and so may be present in the final product.

When preparing a fast dissolving dosage form of the invention using the main matrix forming agent levan without adding secondary matrix forming agents, an annealing process (temperature shifts) may be used during the lyophilization process in order to smoothen the surface of the dosage form. Such an annealing step is carried out for an esthetic purpose only and has no influence on the dissolution time nor on the tensile strength of the resulting dosage form. When secondary matrix forming agents are present, there is no need for such a smoothing annealing step.

The mould may comprise a series of cylindrical or other shape depressions in it, each of a size corresponding to a desired size of a dosage form to be formed.

In one embodiment, the mould is a depression in a sheet of filmic material. The filmic material may contain more than one depression. The filmic material may be similar to that employed in conventional blister packs which are used for packaging oral contraceptive tablets and like medicament forms. For example the filmic material may be made of thermoplastic material with the depressions formed by thermoforming or coldforming. Polyvinyl chloride film can be used as filmic material. Laminates of filmic material may also be used.

EXAMPLES

The invention is further described in the following examples, which are not in any way intended to limit the scope of the inventions as claimed.

A. Materials Used in the Examples Presented Below

| Material | Obtained from |
| --- | --- |
| Levan (*Zymomonas* spp.) | RealBiotech, Korea |
| Levan (*Bacilus* spp.) | Montana Polysaccharides, USA |
| Citric acid | Merck, India |
| Mannitol | Merck, India |
| Desmopressin acetate | Manufactured by Polypeptide Labs A/S, and supplied by Ferring |
| Loratadine | Ultratech India Ltd |
| Famotidine | Exim Pharma International, India |
| Montelukast Sodium | MSN Pharma Chem Pvt. Ltd., India |
| Ondansetron base | Cadila Pharma Ltd., India |
| Guar gum | Merck, India |
| Sodium lauryl sulphate (SLS) | Merck, India |
| Xanthan gum | SD Fine Chem Ltd., India |
| Sodium citrate | Merck, India |
| Pullulan | Hyashibara, Japan |
| Glycine | Sigma Aldrich |
| Hydropropyl methyl cellulose (HPMC) | Shin-Etsu Chemical Co. Japan |
| Methyl cellulose | Shin-Etsu Chemical Co. Japan |
| Gum tragacanth | Merck, India |
| Fish gelatin | Croda Chemicals Pvt. Ltd, India |
| Sodium methyl paraben | Alta Lab Pvt. Ltd., India |
| Raffinose | Loba Chemie Pvt. Ltd., India |
| Trehalose | Loba Chemie Pvt, Ltd., India |
| Sodium propyl paraben | Prayosha Healthcare, India |
| Hydroxy propyl β cyclodextrin | Gangwal Chemicals Pvt. Ltd., India |
| Sodium hydroxide | Merck, India |
| Neotame | Nutrasweet, USA |
| Strawberry flavour | Virginia Dare, USA |
| Cherry flavour | Virginia Dare, USA |

B. Method for Preparing Placebo Formulation

1) Dissolve Levan, and other excipients, if present, in purified water under stirring at 200 to 500 revolutions per minute (rpm).
2) Optionally adjust the pH of the solution using citric acid solution or NaOH.
3) Make up the final volume of the solution using purified water.
4) Mix the solution under stirring at 200 to 500 rpm for 15 minutes.
5) Dose the solution into each cavity of preformed blister sheets (typically using dispensing pipette).
6) Freeze the filled blisters at a temperature in the range of −20 to −110° C.
7) Freeze dry the blisters in a lyophilizer
8) Place the blister sheet containing dried lyophilisates on the punched carrier web of a blister packaging machine to transport the blister sheets through the sealing station of the packaging machine.
9) Seal the blisters with a lidding foil and punch into final blisters.

C1. Formulations

The following formulations were prepared using the method described in the method section "B" above, by freezing the blisters at the rate of 0.1-2° C./minute in step 6.

Example—1

| Component | Amount/unit | % w/w |
| --- | --- | --- |
| Levan (*Bacilus* xpp.) | 25 mg | 100 |
| Purified water | q.s to 250 µl | — |

Example—2

| Component | Amount/unit | % w/w |
| --- | --- | --- |
| Levan (*Zymomonas* spp.) | 25 mg | 100 |
| Purified water | q.s to 250 µl | — |

Example—3

| Component | Amount/unit | % w/w |
| --- | --- | --- |
| Levan (*Bacilus* spp.) | 37.5 mg | 100 |
| Purified water | q.s to 250 µl | — |

Example—4

| Component | Amount/unit | % w/w |
| --- | --- | --- |
| Levan (*Zymomonas* spp.) | 37.5 mg | 100 |
| Purified water | q.s to 250 µl | — |

Example—5

| Component | Amount/unit | % w/w |
| --- | --- | --- |
| Levan (*Zymomonas* spp.) | 18.75 mg | 100 |
| Purified water | q.s to 250 µl | — |

Example—6

| Component | Amount/unit | % w/w |
|---|---|---|
| Levan (*Zymomonas* spp.) | 12.5 mg | 100 |
| Purified water | q.s to 250 µl | — |

Example—7

| Component | Amount/unit | % w/w |
|---|---|---|
| Levan (*Zymomonas* spp.) | 18.75 mg | 99.99 |
| Citric acid (5% w/v) | q.s to pH 4.5 | q.s to pH 4.5 |
| Purified water | q.s to 250 µl | — |

Example—8

| Component | Amount/unit | % w/w |
|---|---|---|
| Levan (*Zymomonas* spp.) | 18.75 mg | 99.99 |
| Citric acid (5% w/v) | q.s to pH 5.0 | q.s to pH 5.0 |
| Purified water | q.s to 250 µl | — |

Example—9

| Component | Amount/unit | % w/w |
|---|---|---|
| Levan (*Zymomonas* spp.) | 25 mg | 99.99 |
| 0.1N NaOH | q.s to pH 7.0 | q.s to pH 7.0 |
| Purified water | q.s to 250 µl | — |

Example—10

| Component | Amount/unit | % w/w |
|---|---|---|
| Levan (*Zymomonas* spp.) | 25 mg | 99.99 |
| 0.1N NaOH | q.s to pH 8.0 | q.s to pH 8.0 |
| Purified water | q.s to 250 µl | — |

Example—11

| Component | Amount/unit | % w/w |
|---|---|---|
| Levan (*Zymomonas* spp.) | 25 mg | 99.99 |
| 0.1N NaOH | q.s to pH 9.0 | q.s to pH 9.0 |
| Purified water | q.s to 250 µl | — |

Example—12

| Component | Amount/unit | % w/w |
|---|---|---|
| Levan (*Zymomonas* spp.) | 18.75 mg | 75 |
| Mannitol | 6.25 mg | 25 |
| Purified water | q.s to 250 µl | — |

Example—13

| Component | Amount/unit | % w/w |
|---|---|---|
| Levan (*Zymomonas* spp.) | 12.5 mg | 50 |
| Mannitol | 12.5 mg | 50 |
| Purified water | q.s to 250 µl | — |

C2. Formulations

The following formulations were prepared using the method described in "B" herein above, by freezing the blisters at a rate of 20-160° C./minute in ≤4 minutes in step 6.

Example—14

| Component | Amount/unit | % w/w |
|---|---|---|
| Levan (*Zymomonas* spp.) | 25 mg | 100 |
| Purified water | q.s to 250 µl | — |

Example—15

| Component | Amount/unit | % w/w |
|---|---|---|
| Levan (*Zymomonas* spp.) | 25 mg | 99.99 |
| Citric acid (5% w/v) | q.s to pH 4.5 | q.s to pH 4.5 |
| Purified water | q.s to 250 µl | — |

Example—16

| Component | Amount/unit | % w/w |
|---|---|---|
| Levan (*Zymomonas* spp.) | 16.25 mg | 64.99 |
| Mannitol | 8.75 mg | 34.99 |
| Citric acid (5% w/v) | q.s to pH 4.0 | q.s to pH 4.0 |
| Purified water | q.s to 250 µl | — |

Example—17

| Component | Amount/unit | % w/w |
|---|---|---|
| Levan (*Zymomonas* spp.) | 16.25 mg | 64.99 |
| Mannitol | 8.75 mg | 34.99 |

-continued

| Component | Amount/unit | % w/w |
|---|---|---|
| Citric acid (5% w/v) | q.s to pH 4.5 | q.s to pH 4.5 |
| Purified water | q.s to 250 µl | — |

Example—18

| Component | Amount/unit | % w/w |
|---|---|---|
| Levan (*Zymomonas* spp.) | 16.25 mg | 64.99 |
| Mannitol | 8.75 mg | 34.99 |
| Citric acid (5% w/v) | q.s to pH 5.0 | q.s to pH 5.0 |
| Purified water | q.s to 250 µl | — |

Example—19

| Component | Amount/unit | % w/w |
|---|---|---|
| Levan (*Zymomonas* spp.) | 12.5 mg | 49.99 |
| Mannitol | 12.5 mg | 49.99 |
| Citric acid (5% w/v) | q.s to pH 4.5 | q.s to pH 4.5 |
| Purified water | q.s to 250 µl | — |

Example—20

| Component | Amount/unit | % w/w |
|---|---|---|
| Levan (*Zymomonas* spp.) | 18.75 mg | 74.99 |
| Mannitol | 6.25 mg | 24.99 |
| Citric acid (5% w/v) | q.s to pH 4.5 | q.s to pH 4.5 |
| Purified water | q.s to 250 µl | — |

Example—21

| Component | Amount/unit | % w/w |
|---|---|---|
| Levan (*Zymomonas* spp.) | 18.75 mg | 75.0 |
| Raffinose | 6.25 mg | 25.0 |
| Purified water | q.s to 250 µl | — |

Example—22

| Component | Amount/unit | % w/w |
|---|---|---|
| Levan (*Zymomonas* spp.) | 18.75 mg | 74.99 |
| Trehalose | 6.25 mg | 24.99 |
| Citric acid (5% w/v) | q.s. to pH 4.5 | q.s to pH 4.5 |
| Purified water | q.s to 250 µl | — |

D. Method for Preparing Dosage Forms Containing Desmopressin

1) Dissolve Levan, and other excipients, if present, in purified water under stirring at 200 to 500 rpm;
2) Dissolve Desmopressin acetate in purified water and add to the solution prepared in step 1.
3) Adjust the pH of the solution using citric acid solution (5% w/v).
4) Make up the final volume of the solution using purified water.
5) Mix the solution under stirring at 200 to 500 rpm for further 5-15 min.
6) Dose the solution into cavities of preformed blister sheets (typically using dispensing pipette).
7) Freeze the filled blisters at a temperature in the range of −20 to −110° C.
8) Freeze dry the blisters in a lyophilizer
9) Place the blister sheet containing dried lyophilisates on the punched carrier web of the blister packaging machine, to transport the blister sheets through the sealing station of the packaging machine.
10) Seal the blister with a lidding foil and punch into final blisters.

E. Desmopressin Formulations

The following desmopressin lyophilisate formulations were prepared using the method described in "D" above, by freezing the blisters at the rate of 0.1-2° C./minute or 20-160° C./minute in step 7.

Example—23

| Component | Amount/unit | % w/w |
|---|---|---|
| Desmopressin acetate equivalent to Desmopressin | 240 µg | 0.63 |
| Levan (*Bacilus* spp.) | 37.5 mg | 99.36 |
| Citric acid (5% w/v) | q.s to pH 4.5 | q.s to pH 4.5 |
| Purified water | q.s to 250 µl | — |

Example—24

| Component | Amount/unit | % w/w |
|---|---|---|
| Desmopressin acetate equivalent to Desmopressin | 240 µg | 1.3 |
| Levan (*Zymomonas* spp.) | 18.75 mg | 98.7 |
| Citric acid (5% w/v) | q.s to pH 4.5 | q.s to pH 4.5 |
| Purified water | q.s to 250 µl | — |

Example—25

| Component | Amount/unit | % w/w |
|---|---|---|
| Desmopressin acetate equivalent to Desmopressin | 240 µg | 1.3 |
| Levan (*Zymomonas* spp.) | 18.75 mg | 98.7 |
| Citric acid (5% w/v) | q.s to pH 5.0 | q.s to pH 5.0 |
| Purified water | q.s to 250 µl | — |

Example—26

| Component | Amount/unit | % w/w |
|---|---|---|
| Desmopressin acetate equivalent to Desmopressin | 240 µg | 0.95 |

| Component | Amount/unit | % w/w |
| --- | --- | --- |
| Levan (*Zymomonas* spp.) | 16.25 mg | 64.4 |
| Mannitol | 8.75 mg | 34.7 |
| Citric acid (5% w/v) | q.s to pH 4.5 | q.s to pH 4.5 |
| Purified water | q.s to 250 μl | — |

Example—27

| Component | Amount/unit | % w/w |
| --- | --- | --- |
| Desmopressin acetate equivalent to Desmopressin | 240 μg | 1.26 |
| Levan (*Zymomonas* spp.) | 18.75 mg | 98.73 |
| Sodium Citrate buffer (2.5 mM) | q.s to pH 4.5 | q.s to pH 4.5 |
| Purified water | q.s to 250 μl | — |

Example—28

| Component | Amount/unit | % w/w |
| --- | --- | --- |
| Desmopressin acetate equivalent to Desmopressin | 240 μg | 1.26 |
| Levan (*Zymomonas* spp.) | 18.75 mg | 98.73 |
| Sodium Citrate buffer (5.0 mM) | q.s to pH 4.5 | q.s to pH 4.5 |
| Purified water | q.s to 250 μl | — |

Example—29

| Component | Amount/unit | % w/w |
| --- | --- | --- |
| Desmopressin acetate equivalent to Desmopressin | 240 μg | 0.79 |
| Levan (*Zymomonas* spp.) | 19.5 mg | 64.48 |
| Mannitol | 10.5 mg | 34.72 |
| Sodium Citrate buffer (5.0 mM) | q.s to pH 4.5 | q.s to pH 4.5 |
| Purified water | q.s to 250 μl | — |

Example—30

| Component | Amount/unit | % w/w |
| --- | --- | --- |
| Desmopressin acetate equivalent to Desmopressin | 60 μg | 0.19 |
| Levan (*Zymomonas* spp.) | 19.5 mg | 64.87 |
| Mannitol | 10.5 mg | 34.93 |
| Citric acid (5% w/v) | q.s to pH 4.5 | q.s to pH 4.5 |
| Purified water | q.s to 250 μl | — |

Example—31

| Component | Amount/unit | % w/w |
| --- | --- | --- |
| Desmopressin acetate equivalent to Desmopressin | 25 μg | 0.08 |
| Levan (*Zymomonas* spp.) | 19.5 mg | 64.94 |
| Mannitol | 10.5 mg | 34.97 |
| Citric acid (5% w/v) | q.s to pH 4.5 | q.s to pH 4.5 |
| Purified water | q.s to 250 μl | — |

Example—32

| Component | Amount/unit | % w/w |
| --- | --- | --- |
| Desmopressin acetate equivalent to Desmopressin | 10 μg | 0.03 |
| Levan (*Zymomonas* spp.) | 19.5 mg | 64.97 |
| Mannitol | 10.5 mg | 34.99 |
| Citric acid (5% w/v) | q.s to pH 4.5 | q.s to pH 4.5 |
| Purified water | q.s to 250 μl | — |

F. Method for Preparing Dosage Forms Containing Loratadine

1) Disperse guar gum in purified water under stirring.
2) Prepare solution of levan and other excipients in water under stirring, and add this solution in the guargum solution obtained in step 1 under stirring at 200-500 rpm.
3) Add loratadine to the solution obtained in step 2 under continuous stirring at 200-500 rpm.
4) Homogenize the Loratadine suspension for 10-20 minutes to form a uniform suspension.
5) Adjust the pH of the suspension using citric acid solution (5% w/v).
6) Make up the final volume of the suspension using purified water.
7) Mix the suspension under stirring at 200 to 500 rpm for further 5-15 min.
8) Dose prepared suspension into each cavity of preformed blister sheets with intermediate stirring of the suspension to maintain uniformity.
9) Freeze the filled blisters at a temperature in the range of −20 to −110° C.
10) Freeze dry the blisters in a lyophilizer
11) Place the blister sheet containing dried lyophilisates on the punched carrier web of the blister packaging machine, to transport the blister sheets through the sealing station of the packaging machine.
12) Seal the blister with a lidding foil and punch into final blisters.

G. Loratadine Formulations

The following Loratidine lyophilisate formulation were prepared using the method described in "F" above, by freezing the blisters at the rate of 0.1-2° C./minute or 20-160° C./minute in step 9.

Example—33

| Component | Amount/unit | % w/w |
| --- | --- | --- |
| Loratadine | 10 mg | 28.5 |
| Levan (*Zymomonas* spp.) | 25 mg | 70.5 |
| Guargum | 0.437 mg | 0.01 |

-continued

| Component | Amount/unit | % w/w |
|---|---|---|
| Citric acid (5% w/v) | q.s to pH 4.3 | q.s to pH 4.3 |
| Purified water | q.s to 350 μl | — |

Example—34

| Component | Amount/unit | % w/w |
|---|---|---|
| Loratadine | 10 mg | 35.8 |
| Levan (*Zymomonas* spp.) | 17.5 mg | 62.6 |
| Guargum | 0.437 mg | 0.01 |
| Citric acid (5% w/v) | q.s to pH 4.8 | q.s to pH 4.8 |
| Purified water | q.s 350 μl | — |

Example—35

| Component | Amount/unit | % w/w |
|---|---|---|
| Loratadine | 10 mg | 35.7 |
| Levan (*Zymomonas* spp.) | 17.5 mg | 62.4 |
| Guargum | 0.437 mg | 0.01 |
| SLS | 0.087 mg | 0.003 |
| Citric acid (5% w/v) | q.s to pH 4.8 | q.s to pH 4.8 |
| Purified water | q.s 350 μl | — |

H. Method for Preparing Dosage Forms Containing Famotidine

1) Disperse xanthan gum or guar gum in purified water under stirring.
2) Dissolve levan in the solution obtained in step 1 under stirring at 200-500 rpm.
3) Add Famotidine to the solution of step 2 under continuous stirring at 200-500 rpm till proper suspension is formed.
4) Homogenize the Famotidine suspension obtained in step 3 for 10 min to form uniform suspension.
5) Adjust the pH of the suspension using 0.1N NaOH.
6) Make up the final volume of the suspension using purified water.
7) Mix the suspension under stirring at 200 to 500 rpm for further 5-15 min.
8) Dose prepared suspension into each cavity of preformed blister sheets with intermediate stirring of the suspension to maintain uniformity.
9) Freeze the filled blisters at a temperature in the range of −20 to −110° C.
10) Freeze dry the blisters in a lyophilizer
11) Place the blister sheet containing dried lyophilisates on the punched carrier web of the blister packaging machine, to transport the blister sheets through the sealing station of the packaging machine.
12) Seal the blister with a lidding foil and punch into final blisters.

I. Famotidine Formulations

The following Famotidine orodispersible dosage forms were prepared using the method described above in "H", by freezing the blisters at the rate of 0.1-2° C./minute or 20-160° C./minute in step 9.

Example—36

| Component | Amount/unit | % w/w |
|---|---|---|
| Famotidine | 20 mg | 65.5 |
| Levan (*Zymomonas* spp.) | 10.5 mg | 34.4 |
| Xanthangum | 0.023 mg | 0.07 |
| 0.1N NaOH | q.s to pH 8.0 | q.s to pH 8.0 |
| Purified water | q.s 250 μl | — |

Example—37

| Component | Amount/unit | % w/w |
|---|---|---|
| Famotidine | 20 mg | 60.8 |
| Levan (*Zymomonas* spp.) | 12.5 mg | 38.0 |
| Xanthangum | 0.37 mg | 1.1 |
| 0.1N NaOH | q.s to pH 8.0 | q.s to pH 8.0 |
| Purified water | q.s 250 μl | — |

Example—38

| Component | Amount/unit | % w/w |
|---|---|---|
| Famotidine | 20 mg | 65.10 |
| Levan (*Zymomonas* spp.) | 10.5 mg | 34.18 |
| Xanthangum | 0.219 mg | 0.71 |
| 0.1N NaOH | q.s to pH 8.0 | q.s to pH 8.0 |
| Purified water | q.s 250 μl | — |

Example—39

| Component | Amount/unit | % w/w |
|---|---|---|
| Famotidine | 40 mg | 88.03 |
| Levan (*Zymomonas* spp.) | 5 mg | 11.00 |
| Guar gum | 0.437 mg | 0.96 |
| 0.1N NaOH | q.s to pH 8.0 | q.s to pH 8.0 |
| Purified water | q.s 250 μl | — |

J. Method for Preparing Dosage Forms Containing Montelukast Sodium

1) Dissolve Montelukast in purified water under stirring.
2) Dissolve Levan, and other excipients if present, in the Montelukast solution of step 1 under stirring at 200-500 rpm.
3) Make up the final volume of the solution using purified water.
4) Mix the solution under stirring at 200 to 500 rpm for further 15 min.
5) Dose the solution into each cavity of preformed blister.
6) Freeze the filled blisters at a temperature in the range of −60 to −80° C.
7) Freeze dry the blisters in a lyophilizer
8) Place the blister sheet containing dried lyophilisates on the punched carrier web of the blister packaging machine, to transport the blister sheets through the sealing station of the packaging machine.
9) Seal the blister with a lidding foil and punch into final blisters.

K. Montelukast Sodium Formulations

The following Montelukast orodispersible dosage forms were prepared using the method described in "J" above, by freezing the blisters at the rate of 0.1-2° C./minute or 20-160° C./minute in step 6.

Example—40

| Component | Amount/unit | % w/w |
| --- | --- | --- |
| Montelukast Sodium equivalent to Montelukast | 10 mg | 28.57 |
| Levan | 25 mg | 71.42 |
| Purified water | q.s to 250 μl | — |

Example—41

| Component | Amount/unit | % w/w |
| --- | --- | --- |
| Montelukast Sodium equivalent to Montelukast | 10 mg | 28.57 |
| Levan | 18.75 mg | 53.57 |
| Mannitol | 6.25 mg | 17.85 |
| Purified water | q.s to 250 μl | — |

Example—42

| Component | Amount/unit | % w/w |
| --- | --- | --- |
| Montelukast Sodium equivalent to Montelukast | 10 mg | 27.93 |
| Levan | 18.75 mg | 52.37 |
| Mannitol | 6.25 mg | 17.45 |
| Neotame | 0.3 mg | 0.83 |
| Cherry flavour | 0.5 mg | 1.39 |
| Purified water | q.s to 250 μl | — |

Example—43

| Component | Amount/unit | % w/w |
| --- | --- | --- |
| Montelukast Sodium equivalent to Montelukast | 10 mg | 27.93 |
| Levan | 18.75 mg | 52.37 |
| Mannitol | 13.5 mg | 17.45 |
| Hydroxy Propyl β-cyclodextrin | 11.3 mg | |
| Neotame | 0.3 mg | 0.83 |
| Cherry flavour | 0.5 mg | 1.39 |
| Purified water | q.s to 250 μl | — |

Example—44

| Component | Amount/unit | % w/w |
| --- | --- | --- |
| Montelukast Sodium equivalent to Montelukast | 10 mg | 17.84 |
| Levan | 18.75 mg | 33.45 |
| Mannitol | 14.0 mg | 24.97 |
| Trehalose | 12.5 mg | 22.30 |
| Neotame | 0.3 mg | 0.53 |
| Cherry flavour | 0.5 mg | 0.89 |
| Purified water | q.s to 250 μl | — |

Example—45

| Component | Amount/unit | % w/w |
| --- | --- | --- |
| Montelukast Sodium equivalent to Montelukast | 4.0 mg | 13.64 |
| Levan | 18.75 mg | 63.94 |
| Mannitol | 6.25 mg | 21.31 |
| Neotame | 0.12 mg | 0.41 |
| Cherry flavour | 0.2 mg | 0.68 |
| Purified water | q.s to 250 μl | — |

Example—46

| Component | Amount/unit | % w/w |
| --- | --- | --- |
| Montelukast Sodium equivalent to Montelukast | 4.0 mg | 8.06 |
| Levan | 18.75 mg | 37.82 |
| Mannitol | 14.0 mg | 28.24 |
| Trehalose | 12.5 mg | 25.21 |
| Neotame | 0.12 mg | 0.24 |
| Cherry flavour | 0.2 mg | 0.41 |
| Purified water | q.s to 250 μl | — |

Example—47

| Component | Amount/unit | % w/w |
| --- | --- | --- |
| Montelukast Sodium equivalent to Montelukast | 5.0 mg | 9.89 |
| Levan | 18.75 mg | 37.08 |
| Mannitol | 14.0 mg | 27.68 |
| Trehalose | 12.5 mg | 24.72 |
| Neotame | 0.12 mg | 0.23 |
| Cherry flavour | 0.2 mg | 0.39 |
| Purified water | q.s to 250 μl | — |

L. Method for Preparing Dosage Forms Containing Ondansetron

1) Dissolve levan, mannitol, methyl parabens, propyl parabens, pH adjusting agent, sweeteners and/or flavours in purified water under stirring.
2) Disperse Ondansetron under stirring at 200-500 rpm in the solution obtained in step 1.
3) Make up the final volume of the solution using purified water.
4) Mix the solution under stirring at 200 to 500 rpm for further 15 minutes.
5) Dose the solution into each cavity of preformed blister.
6) Freeze the filled blisters at a temperature in the range of −60 to −80° C.
7) Freeze dry the blisters in a lyophilizer.

8) Place the blister sheet containing dried lyophilisates on the punched carrier web of the blister packaging machine, to transport the blister sheets through the sealing station of the packaging machine.
9) Seal the blister with a lidding foil and punch into final blisters.

M. Ondansetron Formulations

The following Ondansetron orodispersible dosage forms were prepared using the method described in "L" above, by freezing the blisters at the rate of 0.1-2° C./minute or 20-160° C./minute in step 6.

Example—48

| Component | Amount/unit | % w/w |
|---|---|---|
| Ondansetron | 8.0 mg | 20.64 |
| Levan | 24.0 mg | 61.94 |
| Mannitol | 6.25 mg | 16.12 |
| Methyl paraben | 0.133 mg | 0.34 |
| Propyl paraben | 0.016 mg | 0.04 |
| Neotame | 0.1 mg | 0.26 |
| Strawberry flavour | 0.25 mg | 0.64 |
| Purified water | q.s to 250 µl | — |

Example—49

| Component | Amount/unit | % w/w |
|---|---|---|
| Ondansetron | 8.0 mg | 20.72 |
| Levan | 24.0 mg | 62.18 |
| Mannitol | 6.25 mg | 16.19 |
| Neotame | 0.1 mg | 0.26 |
| Strawberry flavour | 0.25 mg | 0.65 |
| 0.1N NaOH | q.s to pH 8.0 | q.s to pH 8.0 |
| Purified water | q.s to 250 µl | — |

N. Comparative Examples

Example—50

Comparative lyophilisates were prepared according to the method described in "B" herein above, but using pullulan in place of levan and freezing the blisters at the rate of 20-260° C./minute in ≤4 minutes in step 6.

| Component | Amount/unit | % w/w |
|---|---|---|
| Pullulan | 25 mg | 100 |
| Purified water | q.s 250 µl | — |

Example—51

Comparative lyophilisates were prepared according to the method described in "B" herein above, but taking HPMC in place of levan and freezing the blisters at the rate of 0.1-2° C./minute in step 6.

| Component | Amount/unit | % w/w |
|---|---|---|
| HPMC | 25 mg | 100 |
| Purified water | q.s 250 µl | — |

Example—52

Comparative lyophilisates were prepared according to the method described in "B" herein above, but taking HPMC in place of levan and freezing the blisters at the rate of 20-160° C./minute in ≤4 minutes in step 6.

| Component | Amount/unit | % w/w |
|---|---|---|
| HPMC | 25 mg | 100 |
| Purified water | q.s 250 µl | — |

Example—53

Comparative lyophilisates were prepared according to the method described in "B" herein above, but taking methyl cellulose in place of levan and freezing the blisters at the rate of 0.1-2° C./minute in step 6.

| Component | Amount/unit | % w/w |
|---|---|---|
| Methyl cellulose | 25 mg | 100 |
| Purified water | q.s 250 µl | — |

Example—54

Comparative lyophilisates were prepared according to the method described in "B" herein above, but taking methyl cellulose in place of levan and freezing the blisters at the rate of 20-160° C./minute in ≤4 minutes in step 6.

| Component | Amount/unit | % w/w |
|---|---|---|
| Methyl cellulose | 25 mg | 100 |
| Purified water | q.s 250 µl | — |

Example—55

Comparative lyophilisates were prepared according to the method described in "B" herein above, but taking gum tragacanth in place of levan and freezing the blisters at the rate of 0.1-2° C./minute in step 6.

| Component | Amount/unit | % w/w |
|---|---|---|
| Gum tragacanth | 25 mg | 100 |
| Purified water | q.s 250 µl | — |

Example—56

Comparative lyophilisates were prepared according to the method described in "B" herein above, but taking gum tragacanth in place of levan and freezing the blisters at the rate of 20-160° C./minute in ≤4 minutes in step 6.

| Component | Amount/unit | % w/w |
|---|---|---|
| Gum tragacanth | 25 mg | 100 |
| Purified water | q.s 250 µl | — |

Example—57

Comparative lyophilisates were prepared according to the method described in "B" herein above, but taking Fish gelatin in place of levan and freezing the blisters at the rate of 0.1-2° C./minute in step 6.

| Component | Amount/unit | % w/w |
|---|---|---|
| Fish gelatin | 25 mg | 100 |
| Purified water | q.s 250 μl | — |

The lyophilisates obtained were very fragile and were broken into smaller pieces. No further analysis could be carried out.

Example—58

Comparative lyophilisates were prepared according to the method described in "B" herein above, but taking Fish gelatin in place of levan and freezing the blisters at the rate of 20-160° C./minute in ≤4 minutes in step 6.

| Component | Amount/unit | % w/w |
|---|---|---|
| Fish gelatin | 25 mg | 100 |
| Purified water | q.s 250 μl | — |

Example—59

Comparative lyophilisates were prepared according to the method described in "B" herein above, but taking Fish gelatin in place of levan and freezing the blisters at the rate of 0.1-2° C./minute in step 6.

| Component | Amount/unit | % w/w |
|---|---|---|
| Fish gelatin | 12.5 mg | 50 |
| Mannitol | 12.5 mg | 50 |
| Purified water | q.s 250 μl | — |

Example—60

Comparative lyophilisates were prepared according to the method described in "B" herein above, but taking fish gelatin in place of levan and freezing the blisters at the rate of 20-160° C./minute in ≤4 minutes in step 6.

| Component | Amount/unit | % w/w |
|---|---|---|
| Fish gelatin | 12.5 mg | 50 |
| Mannitol | 12.5 mg | 50 |
| Purified water | q.s 250 μl | — |

O. Disintegration Tests
Oa. Disintegration Test in Petri Dish

This test measures the expected disintegration time of a composition of the invention in an aqueous medium which is an indication of its disintegration time in saliva.

The disintegration rate of all the lyophilisates on a wet filter paper was determined according to the method described in PCT application WO2009002084, page 12 paragraph 129, wherein the test was performed at a temperature of about 25±2° C.

Ob. Measurement of Oral Dissolving Time (ODT) of Placebos

The dissolving time of the placebo lyophilisates in the oral cavity was determined according to the method described in PCT application WO2009002084, page 12 paragraph 132, wherein the lyophilisate was placed on the tongue of a healthy human adult and then measuring the time for it to completely dissolve while rubbing the lyophilisates between the tongue and the upper palate. The mean ODT was calculated from the data obtained from 5 healthy human adults.

P. Method for Testing Disintegration Time (Invitro DT)

This test measures the disintegration time of the compositions of the invention in aqueous medium which is an indication of their disintegration time in saliva.

Equipment: Electrolab, Model: ED2 SAPO

Procedure: The method was followed as per USP 31-NF 26 (General Chapters, <701>Disintegration) and Ph Eur. 1997 (2.9.1. Disintegration of tablets and capsules).

Water was filled into the beaker and maintained at 37° C.±0.5° C. using water bath. The lyophilisates were placed in sinker made up of copper wire with diameter of about 0.5 mm (±0.05 mm) and length of about 15 mm. The lyophilisates were then placed into the basket of basket rack assembly and instrument was set on. The disintegration time was noted in seconds.

Q. Method testing Tensile Strength for

Equipment: Engineering Systems (NOTTM) Ltd, Model: 5 kN Testing Machine

Procedure: The method for determining tensile strength was fed into the instrument.

The parameters test speed (15 mm/min), fracture mode, unit (Newton, [N]); fracture percentage (80%), low limit (0.1), and distance between the supporting edges (4.5 mm) were set into the instrument. A load cell of 10 kg was used and the tensile strength was calculated using the following formula:

$$N/mm2 = \frac{3 \times \text{Mean (N)} \times \text{Distance between two supporting axis in mm}}{2 \times (\text{Thickness in mm})^2 \times (\text{Diameter in mm})}$$

Thickness and diameter were determined using vernier calliper.

Tensile strength of commercially available Nimulid-MD, an orodispersible tablet of Nimesulide prepared by conventional compression technique was found to be 1.14 N/mm².

R. Dissolution Method

This test measures the dissolution (%) of an active ingredient from a composition of the invention in aqueous medium which is an indication of the release rate of the active ingredient from the composition.

Equipment: Varian, Model: VK7025

Procedure: The dissolution time of the lyophilisates containing an active ingredient was measured as follows: The method was followed as per USP 32-NF 27 (General Chapters, <711>Dissolution). Dissolution media (0.1N HCl, Phosphate buffer pH 6.8, Acetate buffer pH 4.5, or 0.5% SLS in water) was selected on the basis of the active ingredient in the composition. Dissolution bowls were filled with appropriate media volume (500 mL or 900 mL) on the basis of the active ingredient in the composition and the temperature of the media was maintained at 37° C.±0.5° C. using water bath. The apparatus used was USP type II (Paddle) and set at the required rpm (50 rpm) as per the test procedure. Samples were withdrawn as per the time point (5 min, 10 min, 15 min, and 30 min) defined in the test procedure. Samples were analyzed chromatographically or by UV as per the test procedure and % release was calculated.

The disintegration rates, ODT, in-vitro DT, tensile strength and Dissolution data for the lyophilisates prepared according to examples 1 to 37, and comparative examples 38 to 48 are presented in table 1.

TABLE 1

| Example No | Disintegration test in petri dish (sec) | Oral dissolving time (sec) | In-vitro DT (sec) | Tensile strength (N/mm$^2$) | Dissolution (5/15 minutes) (%) |
|---|---|---|---|---|---|
| 1 | 7 | 5 | 5 | 1.07 | NA |
| 2 | 4 | 6 | 2 | 1.58 | NA |
| 3 | 5 | 6 | 4 | 1.41 | NA |
| 4 | 8 | 7 | 5 | 1.38 | NA |
| 5 | 3 | 5 | 4 | 0.61 | NA |
| 6 | 2 | 2 | 3 | 0.22 | NA |
| 7 | 4 | 5 | 3 | 0.64 | NA |
| 8 | 5 | 5 | 3 | 0.73 | NA |
| 9 | 2 | 3 | 4 | 0.22 | NA |
| 10 | 2 | 4 | 4 | 0.21 | NA |
| 11 | 2 | 4 | 5 | 0.18 | NA |
| 12 | 3 | 4 | 3 | 0.44 | NA |
| 13 | 5 | 4 | 2 | 0.23 | NA |
| 14 | 2 | 4 | 3 | 0.32 | NA |
| 15 | 4 | 6 | 2 | 0.27 | NA |
| 16 | 2 | 4 | 4 | 0.09 | NA |
| 17 | 3 | 3 | 3 | 0.07 | NA |
| 18 | 4 | 3 | 3 | 0.09 | NA |
| 19 | 5 | 4 | 3 | 0.07 | NA |
| 20 | 2 | 4 | 4 | 0.16 | NA |
| 21 | 2 | 2 | 2 | 0.16 | NA |
| 22 | 2 | 3 | 4 | 0.10 | NA |
| 23 | 2 | NA | 3 | 0.32 | 98/99 |
| 24 | 6 | NA | 4 | 0.78 | 85/96 |
| 25 | 6 | NA | 3 | 0.64 | 99/99 |
| 26 | 4 | NA | 3 | 0.10 | 76/92 |
| 27 | 4 | NA | 3 | 0.84 | 87/95 |
| 28 | 4 | NA | 3 | 0.53 | 102/102 |
| 29 | 3 | NA | 3 | 0.09 | 102/92 |
| 30 | 3 | NA | 2 | 0.15 | 99/101 |
| 31 | 3 | NA | 2 | 0.13 | 93/95 |
| 32 | 3 | NA | 2 | 0.17 | 103/103 |
| 33 | 6 | NA | 7 | 0.68 | 102/103 |
| 34 | 3 | NA | 6 | 0.37 | 100/101 |
| 35 | 2 | NA | 3 | 0.19 | 100/102 |
| 36 | 6 | NA | 8 | 0.34 | 69/89 |
| 37 | 5 | NA | 2 | 0.34 | 68/85 |
| 38 | 6 | NA | 2 | 0.38 | 61/92 |
| 39 | 5 | NA | 9 | 0.19 | 51/75 |
| 40 | 6 | NA | 9 | 0.28 | 97/100 |
| 41 | 5 | NA | 6 | 0.12 | 93/92 |
| 42 | 4 | NA | 4 | 0.08 | 97/97 |
| 43 | 4 | NA | 2 | 0.14 | 97/97 |
| 44 | 5 | NA | 2 | 0.16 | 97/97 |
| 45 | 3 | NA | 2 | 0.08 | 97/98 |
| 46 | 4 | NA | 2 | 0.12 | 99/98 |
| 47 | 3 | NA | 2 | 0.20 | 96/96 |
| 48 | 2 | NA | 2 | 0.09 | 101/12 |
| 49 | 2 | NA | 2 | 0.10 | 101/19 |
| 50 | 32 | 30 | 196 | 0.80 | NA |
| 51 | 150 | 39 | 124 | 0.97 | NA |
| 52 | 35 | 51 | 128 | 0.27 | NA |
| 53 | >300 | 190 | >30 minutes | <0.05 | NA |
| 54 | >300 | 192 | >30 minutes | <0.05 | NA |
| 55 | 25 | 22 | 40 | <0.05 | NA |
| 56 | 36 | 30 | 20 | <0.05 | NA |
| 58 | 2 | 5 | <2 | <0.05 | NA |
| 59 | 2 | 3 | <2 | 0.15 | NA |
| 60 | 2 | 4 | <2 | 0.06 | NA |

NA—Not Applicable for column 3 as the oral dissolving time was measured for placebo lyophilisates only.
NA—Not applicable for column 6 as the dissolution time was measured for lyophilisate containing drug substances only.

S. Pharmacokinetic Test

A comparative test was carried out to evaluate the pharmacokinetic profile of the composition of Example 26 (240 µg desmopressin acetate, levan and mannitol) (the test composition) with a reference composition comprising 240 µg desmopressin acetate, fish gelatin and mannitol (Minirin Melt®). The test was carried out in parallel design by single sublingual administration of the respective compositions to eight New Zealand rabbits in each treatment group. Blood samples were taken at specified time intervals from each treatment group and analyzed for Desmopressin content.

The pharmacokinetic parameters were calculated for individual rabbits using non-compartmental analysis. The rate and extent of absorption of Desmopressin were similar in test and reference compositions, and the test by reference ratio of $C_{max}$ (peak or maximum concentration) and $AUC_{last}$ (Area Under Curve computed up to last sampling time) were within 20% of reference composition. Further, $C_{max}$ for the test composition was higher in comparison to the reference composition.

The invention claimed is:

1. A pharmaceutical composition comprising:
   (a) at least one matrix-forming agent that is levan to form an open matrix network comprised of water-soluble or water-dispersible matrix-forming levan having interstices dispersed throughout, wherein the levan ranges from 30% to 85% of the entire weight of the composition; and
   (b) at least one pharmaceutically active ingredient carried by the open matrix network,
   wherein at least 80% of the composition dissolves within 10 seconds upon contact with an aqueous solution or with saliva, and the composition is an orodispersible pharmaceutical dosage form.

2. The pharmaceutical composition according to claim 1, further comprising one or more secondary matrix-forming agents.

3. The pharmaceutical composition according to claim 2, wherein the one or more secondary matrix-forming agents is selected from the group consisting of trehalose, raffinose, and mannitol.

4. The pharmaceutical composition according to claim 2, wherein the one or more secondary matrix-forming agent is mannitol.

5. The pharmaceutical composition according to claim 1, wherein the at least one pharmaceutically active ingredient is chosen from loratidine, famotidine, montelukast sodium, and ondansetron.

6. The pharmaceutical composition according to claim 1, wherein the composition has a tensile strength from about 0.05 to about 1.6 N/mm$^2$.

7. A pharmaceutical composition prepared by a process comprising at least a step of sublimating a solvent from a liquid preparation that comprises:
   (a) at least one matrix-forming agent that is levan to form an open matrix network comprised of water-soluble or water-dispersible matrix-forming levan having interstices dispersed throughout, wherein the levan ranges from 30% to 85% of the entire weight of the composition; and
   (b) at least one pharmaceutically active ingredient carried by the open matrix network,
   wherein at least 80% of the composition dissolves within 10 seconds upon contact with an aqueous solution or with saliva, and the composition is an orodispersible pharmaceutical dosage form.

8. The pharmaceutical composition according to claim 7, wherein the liquid preparation further comprises one or more secondary matrix-forming agents.

9. The pharmaceutical composition according to claim 8, wherein the one or more secondary matrix-forming agent is mannitol.

10. The pharmaceutical composition according to claim 7, wherein the at least one pharmaceutically active ingredient is chosen from loratidine, famotidine, montelukast sodium, and ondansetron.

11. A blister pack having one or more depressions disposed therein, wherein each of the one or more depressions comprises a pharmaceutical composition, the composition comprising:
   (a) at least one matrix-forming agent that is levan to form an open matrix network comprised of water-soluble or water-dispersible matrix-forming levan having interstices dispersed throughout, wherein the levan ranges from 30% to 85% of the entire weight of the composition; and
   (b) at least one pharmaceutically active ingredient carried by the open matrix network,
   wherein at least 80% of the composition dissolves within 10 seconds upon contact with an aqueous solution or with saliva, and the composition is an orodispersible pharmaceutical dosage form.

12. The blister pack according to claim 11 which is prepared by a process comprising steps of:
   (a) introducing a liquid preparation into one or more depressions of a blister pack, the liquid preparation comprising the matrix forming agent and the pharmaceutically active ingredient; and
   (b) sublimating the solvent from the liquid preparation in the one or more depressions.

13. The blister pack according to claim 11, wherein the composition further comprises one or more secondary matrix-forming agents.

14. The blister pack according to claim 13, wherein the one or more secondary matrix-forming agents is selected from the group consisting of trehalose, raffinose, and mannitol.

15. The blister pack according to claim 13, wherein the one or more secondary matrix-forming agent is mannitol.

16. The blister pack according to claim 11, wherein the at least one pharmaceutically active ingredient is chosen from loratidine, famotidine, montelukast sodium, and ondansetron.

17. The pharmaceutical composition according to claim 1, wherein 100% of the composition dissolves within 10 seconds upon contact with an aqueous solution or with saliva within the mouth.

18. The pharmaceutical composition according to claim 7, wherein 100% of the composition dissolves within 10 seconds upon contact with an aqueous solution or with saliva within the mouth.

19. The pharmaceutical composition according to claim 11, wherein 100% of the composition dissolves within 10 seconds upon contact with an aqueous solution or with saliva within the mouth.

* * * * *